United States Patent [19]

Kruger et al.

[11] 4,255,572
[45] Mar. 10, 1981

[54] N,N-DIALKYLUREIDOMETHANE DIPHOSPHONIC ACID AND ITS PREPARATION

[76] Inventors: Friedrich Kruger, Erzberger Strasse 27, 6803 Edington; Walter Michel, Kallstadter Strasse 10, 6804 Ilvesheim, both of Fed. Rep. of Germany

[21] Appl. No.: 58,806

[22] Filed: Jul. 19, 1979

[30] Foreign Application Priority Data

Sep. 2, 1978 [DE] Fed. Rep. of Germany ....... 2838437

[51] Int. Cl.³ ................................ C07F 9/38; C07F 9/65; C02B 5/06
[52] U.S. Cl. .................................. 544/243; 548/112; 260/502.5; 252/180
[58] Field of Search .................. 544/243; 548/112; 260/502.5

[56] References Cited

U.S. PATENT DOCUMENTS

| | | | |
|---|---|---|---|
| 3,763,281 | 2/1973 | Weil | 260/932 |
| 3,957,160 | 5/1976 | Plöger et al. | 260/502.5 X |
| 3,989,727 | 11/1976 | Birum | 260/502.5 X |
| 4,003,965 | 1/1977 | Birum | 260/932 |
| 4,098,814 | 7/1978 | Sommer et al. | 260/502.5 |
| 4,157,364 | 6/1979 | Buckman et al. | 260/976 |

FOREIGN PATENT DOCUMENTS

| | | |
|---|---|---|
| 2260719 | 6/1974 | Fed. Rep. of Germany . |
| 2254095 | 5/1975 | Fed. Rep. of Germany . |
| 2446749 | 4/1976 | Fed. Rep. of Germany ........ 260/502.5 |
| 2603702 | 8/1977 | Fed. Rep. of Germany ........ 260/502.5 |
| 2745084 | 4/1979 | Fed. Rep. of Germany . |

*Primary Examiner*—Donald G. Daus
*Assistant Examiner*—Diana G. Rivers
*Attorney, Agent, or Firm*—Schwartz, Jeffery, Schwaab, Mack, Blumenthal & Koch

[57] ABSTRACT

Novel N,N'-dialkylureidomethane diphosphonic acids and their alkaline salts having the formula:

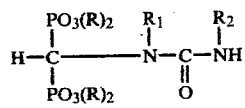

wherein $R_1$ and $R_2$ represent separate alkyl groups having 1 to 3 carbons or a ring forming alkylene group and R is hydrogen or an alkali metal; a novel method for their preparation comprising reacting formic acid with a corresponding N,N'-dialkylurea and phosphorus trichloride and the use of such compounds to prevent the formation of calcareous deposits in water systems.

5 Claims, No Drawings

N,N-DIALKYLUREIDOMETHANE DIPHOSPHONIC ACID AND ITS PREPARATION

Ureidoalkane diphosphonic acids which are unsubstituted at nitrogen are disclosed in German Pat. No. 2 254 095. These phosphonic acids are readily soluble in water, have good complexing capabilities and are also effective in water treatment.

Ureidoalkane diphosphonic acids are obtained by reacting acyl urea with a mixture of phosphoric acid and phosphorus trichloride at temperatures up to 120° C., preferably in the presence of a neutral solvent, or by heating aminoalkane diphosphonic acids with urea in a stream of dry air or nitrogen according to German Auslegsschrift No. 2 446 749. However, both of these processes are disadvantageous for production of such compounds on an industrial scale, and large quantities of the phosphonic acids are difficult to produce.

Now, new, not previously described N,N'-dialkylureidomethane diphosphonic acids and their alkali salts of the general formula

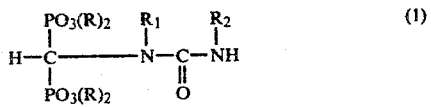

have been discovered, wherein $R_1$ and $R_2$ represent an alkyl group having one to three carbon atoms or a ring forming an alkylene group, and R is hydrogen or an alkali metal.

The new phosphonic acids have a better water treating effect than ureidoalkane diphosphonic acids which are unsubstituted at the nitrogen, and they are also readily soluble in water and can be produced in a simpler and less expensive manner.

The new phosphonic acids further possess a very good complexing capability with respect to bi- and multivalent metal ions, such as calcium, magnesium, iron, chromium, manganese and others. Applied in less than stoichiometric amounts, the new phosphonic acids represent excellent means for the stabilization of water hardness. They may be incorporated in solid and liquid products which are to be used in aqueous media. Furthermore, the new compounds are compatible with conventional detergent ingredients so that they may be used in place of, or together with, polyphosphates as "builders" in detergents and cleaning products. It is anticipated that the new phosphonic acids may be useful in all applications where polyphosphates, or other complexing agents such as ethylenediamine tetraacetic acid, nitrilotriacetic acid are utilized. The amounts required are substantially the same as with prior art water treating agents.

In the following tables, as an example, the advantageous suspending action of N,N'-dimethylureidomethane diphosphonic acid and of N,N'-propyleneureidomethane diphosphonic acid according to the invention are shown in comparison with that of ureidomethane disphosphonic acid which is not substituted at the nitrogene and with aminomethane diphosphonic acid.

To determine the water treatment effect (threshold effect) in the alkaline range, a certain amount of the substance to be tested was dissolved in 1 liter water of 17,5° dH in a 1000 ml glass beaker and 12 g sodium hydroxide were added. The beaker was covered with a watch glass and allowed to stand at room temperature. Subsequently, it was ascertained whether crystals were deposited on a glass rod or at the wall of the glass beaker.

TABLE I

| Stabilizing Effect in the Akaline Range | | | | | | |
|---|---|---|---|---|---|---|
| Phosphonic Acid | Amount mg | 2 | 4 | 6 | 8 | 10 days |
| N,N'-dimethylure- | 3.5 | 0 | — | — | — | — |
| idomethane diphos- | 5.0 | 0 | 0 | — | — | — |
| phonic acid | 10.0 | 0 | 0 | 0 | 0 | — |
| N,N'-propylene- | 3.5 | — | — | — | — | — |
| ureidomethane | 5.0 | 0 | — | — | — | — |
| diphosphonic acid | 10.0 | 0 | 0 | 0 | — | — |
| Ureidomethane- | 3.5 | — | — | — | — | — |
| diphosphonic | 5.0 | — | — | — | — | — |
| acid | 10.0 | 0 | 0 | — | — | — |
| Aminomethane- | 3.5 | — | — | — | — | — |
| diphosphonic | 5.0 | — | — | — | — | — |
| acid | 10.0 | — | — | — | — | — |

0 = no deposition
— = onset of precipitation of calcite crystals

The N,N'-disubstituted ureidomethane diphosphonic acids in the neutral range also have a superior stabilizing effect in comparison to ureidomethane diphosphonic acids which are not substituted at the nitrogens. They are therefore suitable for stabilizing water circulating in cooling systems.

The above-mentioned stabilizing effect in the neutral range is shown in Table II.

For this purpose, 100 ml water of known hardness was mixed with 2,0 mg of the substance to be tested, adjusted to pH 7 and maintained in a warming cabinet at 80° C. for 16 hours. The solution was then made up to 100 ml with distilled water, filtered through a doubled filter paper, and the residual hardness of the filtrate was determined and converted to mval alkaline earth metal ions per liter according to DIN 19640 (1 mval alkaline earth metal ions=2,8° dH).

TABLE II

| Stabilizing Effect in the Neutral Range | | |
|---|---|---|
| Phosphonic Acid | mval alkaline earth | Percentage inhibition |
| N,N'-dimethylureidomethane diphosphonic acid | 6.32 | 96.20 |
| N,N'-dipropyleneureidomethane diphosphonic acid | 6.29 | 95.65 |
| Ureidomethane diphosphonic acid | 4.2 | 63.6 |

The N,N'-dialkylureidomethane diphosphonic acids according to the invention are produced by reacting formic acid with dialkylurea and phosphorus trichloride.

The preparation of phosphonic acids from formic acid is not reported in the literature. Only derivatives of formic acid, for example formamide or HCN, have heretofore been utilized in the preparation of aminomethane diphosphonic acids.

It was therefore surprising that the N,N'-dialkylureidomethane diphosphonic acids may be prepared from the three components: formic acid, dialkyl urea and phosphorus trichloride so smoothly and in such good yields.

Useful N,N'-disubstituted ureas include dimethylurea, diethylurea, dipropylurea, N,N'-ethyleneurea and N,N'-propyleneurea.

The preparation of the new phosphonic acids is advantageously effected by mixing formic acid and the N,N'-disubstituted urea and adding phosphorus trichloride dropwise to the mixture. Preferably, prior to the addition of PCl$_3$, the mixture of formic acid and the N,N'-dialkylurea is heated to approximately 80° C. It is also possible, however, to slowly drip the PCl$_3$ into the mixture without preheating. During the addition of the PCl$_3$, the internal temperature slowly rises to a maximum of 125° C. and then slowly declines. Subsequently the heating is continued until no reflex is observed and the development of gaseous HCl has ceased. A white syrup readily soluble in water is obtained. The syrup may be caused to crystallize with a small amount of water. To obtain complete crystallization, the concentrated aqueous solution may be poured into glacial acetic acid or into an organic solvent such as acetone. The pure white crystalline phosphonic acid is obtained in the process in yields exceeding 80%.

EXAMPLE 1

88.11 g (1.0 mole) of N,N'-dimethyl urea and 88.55 g (1.75 mole) formic acid are combined and heated to 80° C. under vigorous agitation. To this mixture, 151.03 g (1.1 mole) phosphorus trichloride are added dropwise over approximately 30–40 minutes. The internal temperature rises during the process to approximately 125° C. and then declines slowly. After reaching approximately 75° C., heating is continued in a boiling water bath until there is no reflux and the development of gaseous HCl has ceased. A white, foamy syrup in the amount of 175 g is obtained, which is then diluted with 50 ml water. The resulting solution is poured into 300 ml of 100% acetic acid. After a short period of stirring, the pure, white crystals are removed by vacuum filtration. After washing and drying, 116.25 g N,N'-dimethylureidomethane diphosphonic acid are obtained.

The yield is 80.7% of theoretical with respect to PCl$_3$.

Analysis: Calculated: N 10.68%; P 23.66%. Found: N 10.6%; P 23.2%.

Melting point: 187° C.

EXAMPLE 2

100.1 g (1.0 mole) propylene urea and 81.0 g (1.75 mole) formic acid are premixed at 70° C. with agitation. To the reaction mixture, 164.8 g (1.2 mole) phosphorus trichloride are added dropwise over approximately 30 minutes. In the process, the temperature rises to approximately 115° C. and the slowly declines. This is followed by agitation for one hour in a boiling water bath. To the warm solution, 160 ml water are added. The solution may be used directly.

To isolate the phosphonic acid, the aqueous solution is poured into 100% acetic acid. After a brief period of standing the resulting crystals are removed by vacuum filtration, washed and dried.

The yield is 40 g of N,N'-propyleneureidomethane disphosphonic acid.

Analysis: Calculated: N 10.2%; P 22.6%. Found: N 10.0%; P 22.2%.

The foregoing description and examples have been set forth as illustrative of the invention and are not intended to be limiting. Since modifications of the disclosed embodiments may occur to persons skilled in the art, the scope of the invention is to be limited only by the scope of the appended claims.

What is claimed is:

1. N,N'-dialkylureidomethane diphosphonic acids or their alkaline salts having the formula:

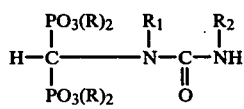

wherein R$_1$ and R$_2$ represent an alkyl group having 1 to 3 carbon atoms or a ring forming alkylene group having 2 or 3 carbon atoms and R is hydrogen or an alkali metal.

2. A process for producing N,N'-dialkylureidomethane diphosphonic acids having the formula:

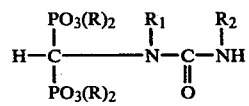

wherein R$_1$ and R$_2$ represent an alkyl group having 1 to 3 carbon atoms or a ring forming alkylene group having 2 or 3 carbon atoms and R is hydrogen or an alkali metal, said method comprising reacting formic acid with a corresponding N,N'-disubstituted urea and phosphorus trichloride.

3. A compound according to claim 1, wherein R$_1$ and R$_2$ are each methyl.

4. A compound according to claim 1, wherein R$_1$ and R$_2$ together represent a ring forming propylene group.

5. A process according to claim 2, wherein said N,N'-disubstituted urea is selected from the group consisting of N,N'-dimethylurea; N,N'-diethylurea; N,N'-dipropylurea; N,N'-ethylene urea and N,N'-propylene urea.

* * * * *